United States Patent [19]

Hattler

[11] Patent Number: 5,207,640
[45] Date of Patent: May 4, 1993

[54] METHOD OF ANESTHETIZING A PATIENT

[76] Inventor: Brack G. Hattler, 5226 Westminster Pl., Pittsburgh, Pa. 15232

[21] Appl. No.: 898,473

[22] Filed: Jun. 15, 1992

Related U.S. Application Data

[63] Continuation-in-part of Ser. No. 676,262, Mar. 27, 1991, Pat. No. 5,122,113.

[51] Int. Cl.⁵ .............................................. A61M 1/00
[52] U.S. Cl. ........................................ 604/28; 604/49; 128/898
[58] Field of Search ..................... 604/23–28, 604/43, 49, 96, 99, 101; 606/192, 194–196; 623/1, 3, 9, 11, 12; 128/DIG. 3, 200.14, 200.21, 203.12, 203.13, 203.25, 207.14, 910, 898; 261/DIG. 28

[56] References Cited

U.S. PATENT DOCUMENTS

| | | | |
|---|---|---|---|
| 3,505,686 | 4/1970 | Bodell | 3/1 |
| 4,334,526 | 6/1982 | Hamacher | 604/49 |
| 4,405,308 | 9/1983 | Jessup | 128/207.14 |
| 4,583,969 | 4/1986 | Mortensen | 604/49 |
| 4,586,921 | 5/1986 | Berson | 604/49 |
| 4,631,053 | 12/1986 | Taheri | 604/49 |
| 4,850,958 | 7/1989 | Berry et al. | 604/26 |
| 4,911,689 | 3/1990 | Hattler | 604/26 |
| 4,950,224 | 8/1990 | Gorsuch et al. | 604/4 |
| 4,986,809 | 1/1991 | Hattler et al. | 604/26 |
| 5,037,383 | 8/1991 | Vaslef et al. | 604/49 |
| 5,072,726 | 12/1991 | Mazloomdoost et al. | 128/200.14 |
| 5,106,376 | 4/1992 | Mononen et al. | 604/49 |
| 5,122,113 | 6/1992 | Hattler | 604/26 |
| 5,146,916 | 9/1992 | Catalani | 128/207.14 |

OTHER PUBLICATIONS

PCT Application No. PCT/US90/07165 (International Publication No. WO 91/069642) Applicant: Cardi7 opulmonics, Inc. International Filing Date: Dec. 6, 1990 (Publ. Date: Jul. 11, 1991.

*Primary Examiner*—Stephen C. Pellegrino
*Assistant Examiner*—Michael Rafa
*Attorney, Agent, or Firm*—Gary M. Polumbus

[57] ABSTRACT

A method of anesthetizing a patient includes the steps of providing a plurality of gas permeable tubes, providing means for injecting an anesthetizing gas onto the tubes, inserting the tubes within a blood vessel of a patient and injecting an anesthetizing gas into the tubes so that the gas can diffuse through the tubes into the blood steam to anesthetize the patient. The anesthetizing gas may be an original source of such gas or a vaporizer may be added to a gas line passing to the gas permeable tubes so that oxygen can be passed through the line and a liquid anesthetic vaporized in the vaporizer so that the oxygen carries the vaporized anesthetic into the tubes.

7 Claims, 4 Drawing Sheets

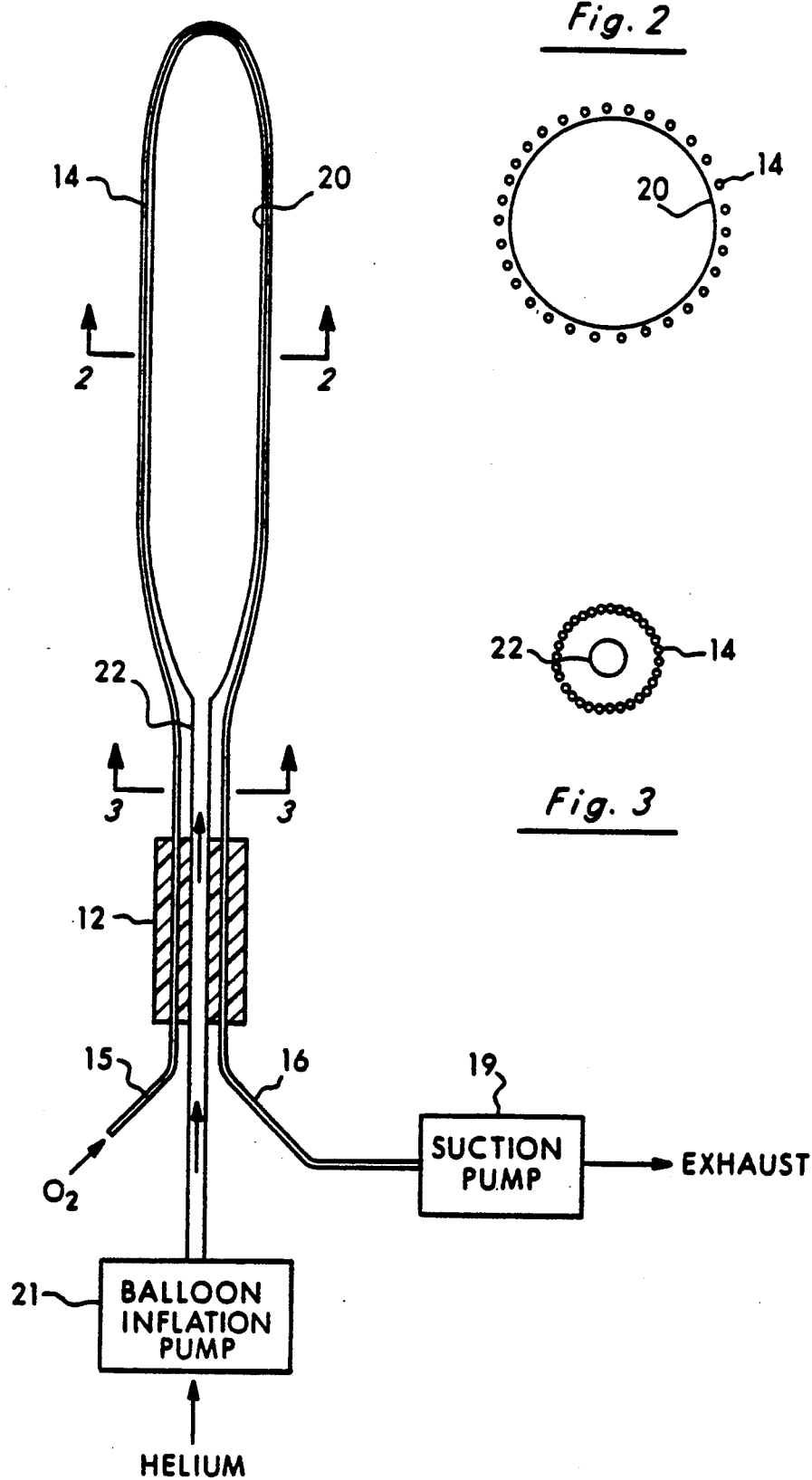

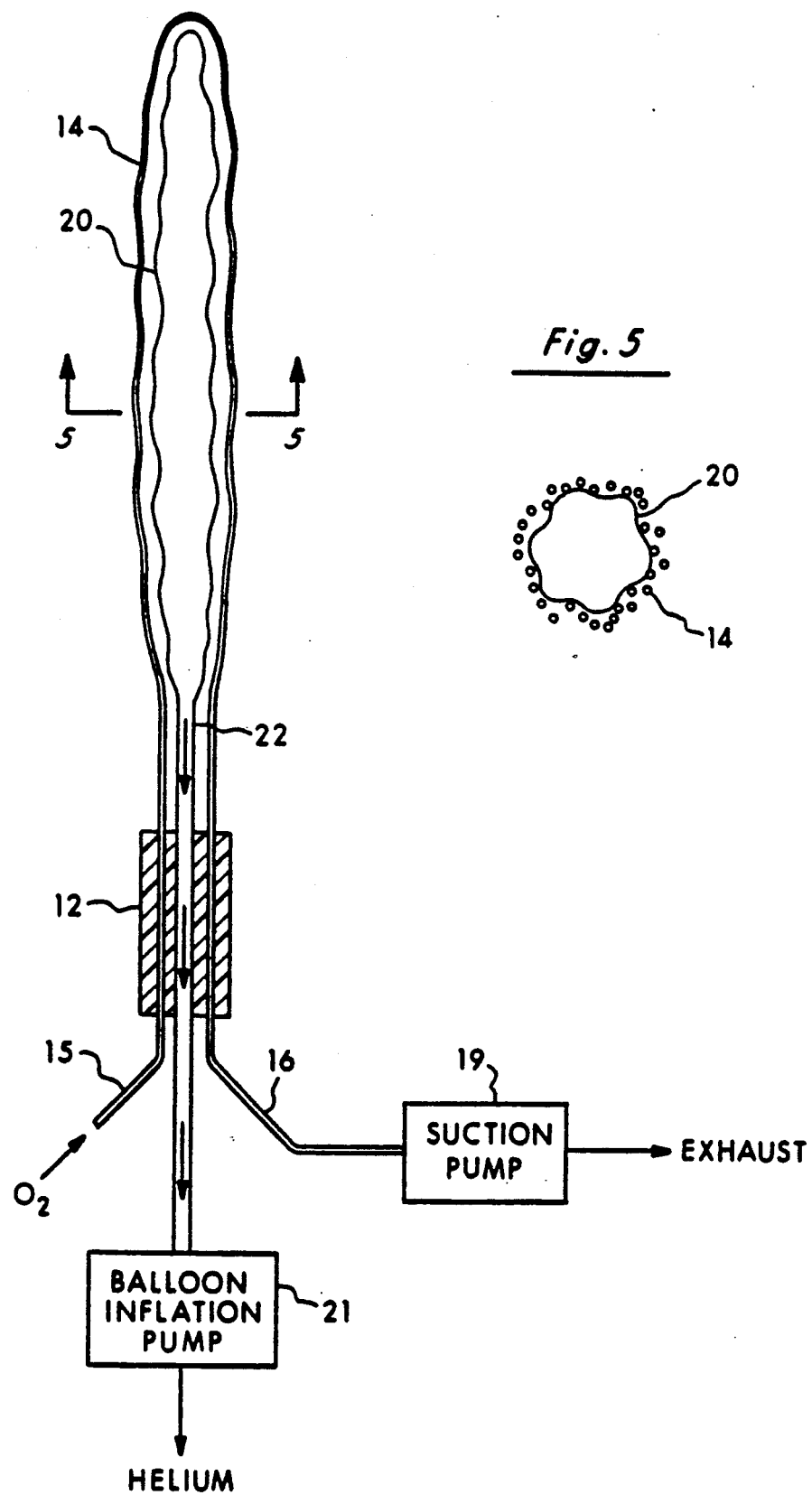

METHOD OF ANESTHETIZING A PATIENT

CROSS-REFERENCE TO RELATED APPLICATION

This application is a continuation-in-part of applicant's co-pending U.S. patent application Ser. No. 07/676,262, entitled "Inflatable Percutaneous Oxygenator" filed on Mar. 27, 1991. Now U.S. Pat. No. 5,122,113.

BACKGROUND OF THE INVENTION

1. Field of the Invention

The present invention relates generally to the field of anesthetizing a patient and more particularly to a method of anesthetizing a patient with the use of a gas delivery device which was previously only known to be used in oxygenating a patient's blood intravenously. The device can be positioned within a patient's body (e.g. in the inferior vena cava, superior vena cava, the right atrium of the heart, or any combination thereof) and then utilized to administer an anesthetic gas directly into the blood stream.

2. Description of the Prior Art

Various methods have been used for many years in anesthetizing a patient so that surgical procedures can be performed without considerable discomfort to the patient. Ether or other gases have been delivered orally to patients, and, in more recent years, anesthetic drugs have been delivered by needles directly into a patient's blood vessel. While these systems have been satisfactory for the purposes intended, there are instances wherein they may add an added level of complexity and possibly discomfort to a patient.

More particularly, in recent years and particularly during open heart surgery or the like wherein it has been necessary to bypass the heart and lungs in order to perform various surgical procedures, the blood has been oxygenated by exposing the blood to various types of oxygenators. One type of oxygenator is commonly referred to as a membrane oxygenator and utilizes a plurality of small fibrous membranes which are gas permeable and positioned in a stream of blood so that oxygen delivered to the interior of the membranes can diffuse through the walls of the membranes into the blood while $CO_2$ from the blood cross diffuses into the interior of the membranes for removal from the device. More recently, membrane oxygenators have been designed for intravenous placement in the interior vena cava of a patient so that the blood can be oxygenated without having to remove it from the body. This latter type of membrane oxygenator is referred to as an intravenous membrane oxygenator and examples of such are disclosed in U.S. Pat. No. 4,911,698 for a PERCUTANEOUS OXYGENATOR invented by Brack G. Hattler; U.S. Pat. No. 4,986,809 for an IMPROVED PERCUTANEOUS OXYGENATOR invented by Hattler, et al.; co-pending application Ser. No. 676,262, filed Mar. 27, 1991 for an INFLATABLE PERCUTANEOUS OXYGENATOR invented by Brack G. Hattler; U.S. Pat. No. 4,583,969 of Mortensen; U.S. Pat. No. 4,850,958 of Berry, et al.; and U.S. Pat. No. 4,631,053 of Taheri. Intravenous membrane oxygenators have been developed exclusively for oxygenating blood intravenously and alternative uses to applicant's knowledge have never been contemplated.

SUMMARY OF THE INVENTION

The present invention relates to a new method of anesthetizing a patient by utilizing a membrane-type gas delivery device commonly referred to as a membrane oxygenator. In the preferred embodiment, the gas delivery device is of the type that is insertable into the vascular system of a patient. More particularly, an intravenous oxygenator of the type disclosed in co-pending application Ser. No. 676,262, filed Mar. 27, 1991, entitled INFLATABLE PERCUTANEOUS OXYGENATOR is believed to be ideally suited for anesthetizing a patient by adding to the flow of oxygen into the oxygenator an anesthetizing gas such as nitrous oxide ($N_2O$) or modifying the intravenous membrane oxygenator by incorporating a vaporizer thereinto so that anesthetic agents can be delivered to the gas intake through the vaporizer.

The method of the present invention includes the steps of providing a plurality of gas permeable fibers into which an anesthetic agent can be introduced, inserting the fibers into the vascular system of a patient, and delivering an anesthetic gas to the interior of the fibers so that the gas can diffuse through the wall of the fibers into the blood stream.

Other aspects, features and details of the present invention can be more completely understood by reference to the following detailed description of a preferred embodiment taken in conjunction with the drawings, and from the appended claims.

BRIEF DESCRIPTION OF THE DRAWINGS

The present invention can be more readily understood in conjunction with the accompanying drawings, in which:

FIG. 1 is a side cross-sectional view of one embodiment of a membrane oxygenator which can be used to practice the method of the present invention.

FIG. 2 is another cross-sectional view taken along plane 2—2 of FIG. 1.

FIG. 3 is yet another cross-sectional view taken along plane 3—3 of FIG. 1.

FIG. 4 is a side cross-sectional view corresponding to FIG. 1 in which a balloon forming a part of the oxygenator has been deflated.

FIG. 5 is another cross-sectional view taken along plan 5—5 of FIG. 4.

DETAILED DESCRIPTION OF THE INVENTION

Figure 6:
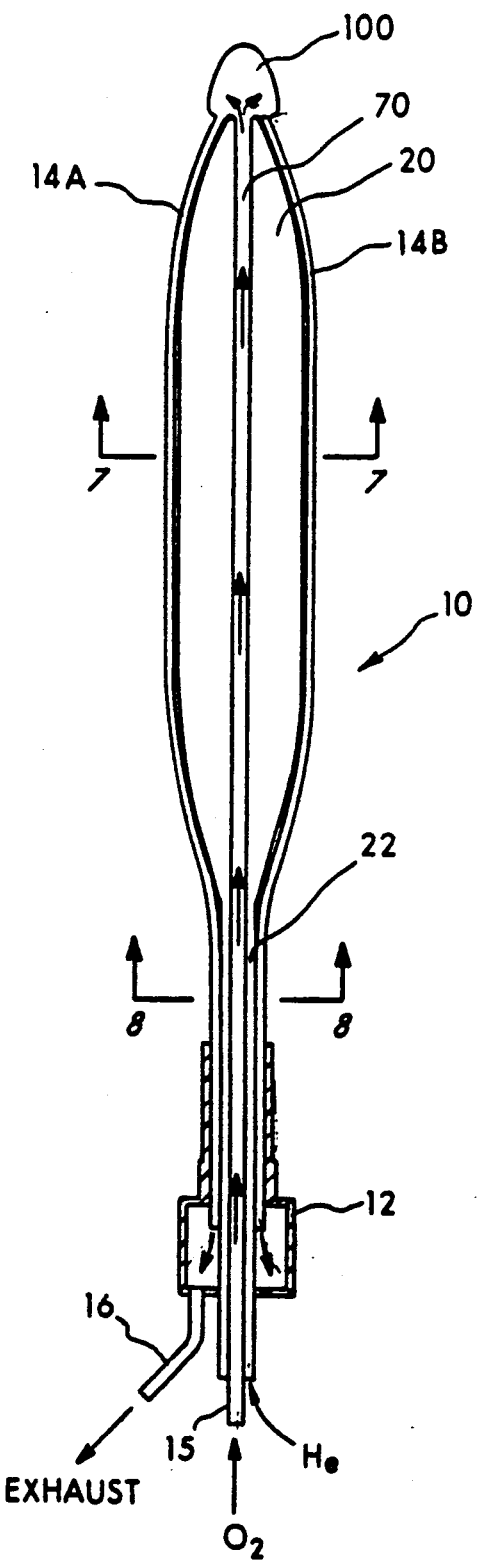
FIG. 6 is a side cross-sectional view of an alternative embodiment of a membrane oxygenator useful in practicing the method of the present invention wherein the oxygenator has a central oxygen supply tube and a hollow tip member.

The method of anesthetizing a patient in accordance with the present invention is accomplished through use of an intravenous membrane gas delivery device such as a membrane oxygenator which may be of the type disclosed in my co-pending application Ser. No. 676,262, filed Mar. 27, 1991 for INFLATABLE PERCUTANEOUS OXYGENATOR. The description of the various embodiments of the oxygenator as described in the pending application, each of which could be used to practice the method of the present invention, follows:

Turning to FIG. 1, a side cross-sectional view of the oxygenator 10 is shown. The major components are an inflatable balloon 20 and a number of gas passageways 14 which substantially surround the balloon 20. In the preferred embodiment, these gas passageways are a multitude of hollow gas-permeable fibers or tubules. The fibers 14 are formed into loops, as shown in FIGS. 1-3, that substantially surround and cover the exterior surface of the balloon 20. The gas-permeable walls of the fibers 14 provide a large total surface area for diffusion of oxygen or an anesthetizing gas into the blood stream, and cross diffusion of carbon dioxide out of the blood stream. Any of a variety of flexible, hollow, gas-permeable fibers currently available on the market, such as Mitsubishi KPF190M polypropylene fibers, are suitable for this purpose. To provide a true ideal membrane, the polypropylene fibers should be coated with silicone rubber and bonded with a non-thrombogenic component.

The balloon 20 and fiber loops 14 of the device are implanted in the venous system of the patient through a single small incision. For example, the device 10 can be implanted through the right interior jugular vein into the superior vena cava of a patient. For maximum effectiveness, the balloon 20 and fiber loops 14 are fully inserted through the incision up to the level of the connector 12. Insertion of the balloon 20 and fiber loops 14 can be aided by using a conventional introducer similar to the type presently employed to insert a cardiac pacemaker.

The connector 12 provides separate lumens to supply and exhaust the fiber loops 14 and for inflation of the balloon 20. An external pump 21 is connected to the balloon inflation lumen 22 of the connector 12 and can be used to repeatedly inflate and deflate the balloon 20 at a predetermined frequency. A frequency of approximately one cycle per second has been experimentally demonstrated to provide satisfactory results in minimizing streaming and maintaining a turbulent flow of blood adjacent to the oxygenator. Any gas or fluid can be pumped into and released from the balloon for this purpose. However, helium offers the advantages of having very low viscosity and density for ease of pumping, and is quickly dissolved in the blood stream in the event helium bubbles leak from the device. In the preferred embodiment, at least a portion of the fiber loops 14 are secured to the exterior surface of the inflation balloon 20 (e.g. by adhesive bonding). This helps to insure that expansion and contraction of the balloon 20 causes movement of the fibers 14 within the blood vessel. FIGS. 1 and 2 provide cross-sectional views of the oxygenator 10 with the balloon 20 fully inflated. In comparison, FIGS. 4 and 5 show the same oxygenator with the balloon 20 deflated.

After the device has been implanted and when used as an oxygenator, a supply of oxygen-containing gas is connected to the second lumen 15 of the connector 12. The oxygen flows through second lumen 15 into the fiber loops 14. Oxygen flows along the interior passageways of the fibers 14 and diffuses outwardly through the gas-permeable walls of the fibers into the surrounding blood stream. Carbon dioxide also diffuses inwardly from the blood stream through these gas-permeable walls into the interior of the fibers. Carbon dioxide and any remaining oxygen in the fibers are vented to the atmosphere at the distal ends of the fibers through a third lumen 16 in the connector 12. Negative pressurization can be applied by means of a suction pump 19 connected to the third lumen 16 to enhance gas flow through the fiber loops.

In accordance with the present invention, it has been discovered that the aforedescribed oxygenator device can be used to administer anesthetic gases or other medications directly into the patient's blood system. For this purpose, an anesthetizing gas can be introduced to the interior of the fibers in place of the oxygen gas such that the anesthetizing gas diffuses through the walls of the fibers into the patient's blood stream.

Figure 7:
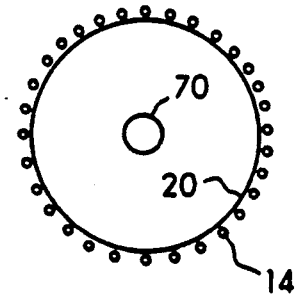
FIG. 7 is another cross-sectional view taken along plane 7—7 of FIG. 6.
Figure 8:
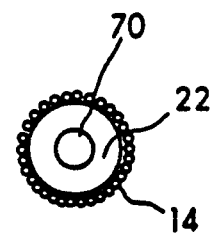
FIG. 8 is another cross-sectional view taken along plan 8—8 of FIG. 6.

FIGS. 6, 7, and 8 show an alternative embodiment of an oxygenator in which a hollow tip member 100 has been added at the distal end of the balloon 20. This embodiment could also be used to anesthetize a patient. A central gas supply tube 70 extends through the connector 12 and the balloon 20 to the interior of the tip member 100. Each of the fiber loops is bisected at its distal point into two arms 14a and 14b. The resulting ends of the fibers are sealed in fluid communication with the internal cavity of the tip 100. The tip member 100 can be molded from plastic or rubber around the ends of the fibers to prevent the escape of gases at the junction between the fiber ends and the tip member 100. The tip can also be shaped with a tapered contour to ease insertion of the device through an incision. Thus, in this embodiment when the device is used as an oxygenator, oxygen-containing gases flow from an external supply through the gas supply tube 70, into the internal cavity of the tip member 100, through both arms 14a and 14b of the fibers, and are then exhausted through the exhaust lumen 16 in the connector 12, as previously described. It should be noted that the gas supply tube 70 and the balloon inflation lumen 22 can be formed as concentric tubes as shown in FIGS. 6 and 8. A cross-sectional view of the upper portion of the balloon 20 and the gas supply tube 70 is provided in FIG. 7. The gas supply tube 70 also acts as a structural support for the tip member 100 and fiber loops 14, and provides a degree of rigidity to aid initial insertion of the device into the blood vessel.

Figure 9:
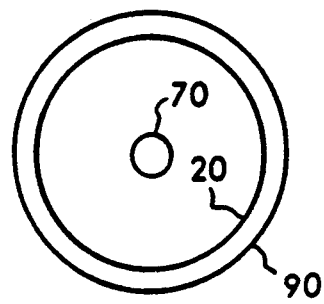
FIG. 9 is a cross-sectional view of still another alternative embodiment of an oxygenator for practicing the method of the present invention in which the hollow fibers surrounding an inflation balloon are replaced with a single gas-permeable membrane.

FIG. 9 discloses another alternative embodiment of an oxygenator which could be used in the method of the present invention to anesthetize a patient. In this embodiment, the fibers 14 have been replaced by a single gas-permeable membrane 90 surrounding the inflation balloon 20. The resulting structure is essentially a balloon within a balloon. As before when the device is used as an oxygenator, oxygen-containing gas is supplied through the gas supply tube 70 to the tip member 100. The oxygen then flows from the tip member 100 back toward the connector 12 through the annular space between the inflation balloon 20 and the outer gas-permeable membrane 90. Cross-diffusion of oxygen and carbon dioxide occurs across the gas-permeable membrane between the annular space and the patient's blood stream, as previously discussed. Repeated inflation and deflation of the inflation balloon 20 causes corresponding movements in the gas-permeable membrane 90 to minimize streaming.

In yet another alternative embodiment of an oxygenator which could be used to practice the method of the present invention, the gas-permeable membrane 90 can be tacked to the exterior surface of the inflation balloon 20 along a number of longitudinal lines to define a plurality of gas passageways extending from the tip member 100 to the connector 12.

Figure 10:
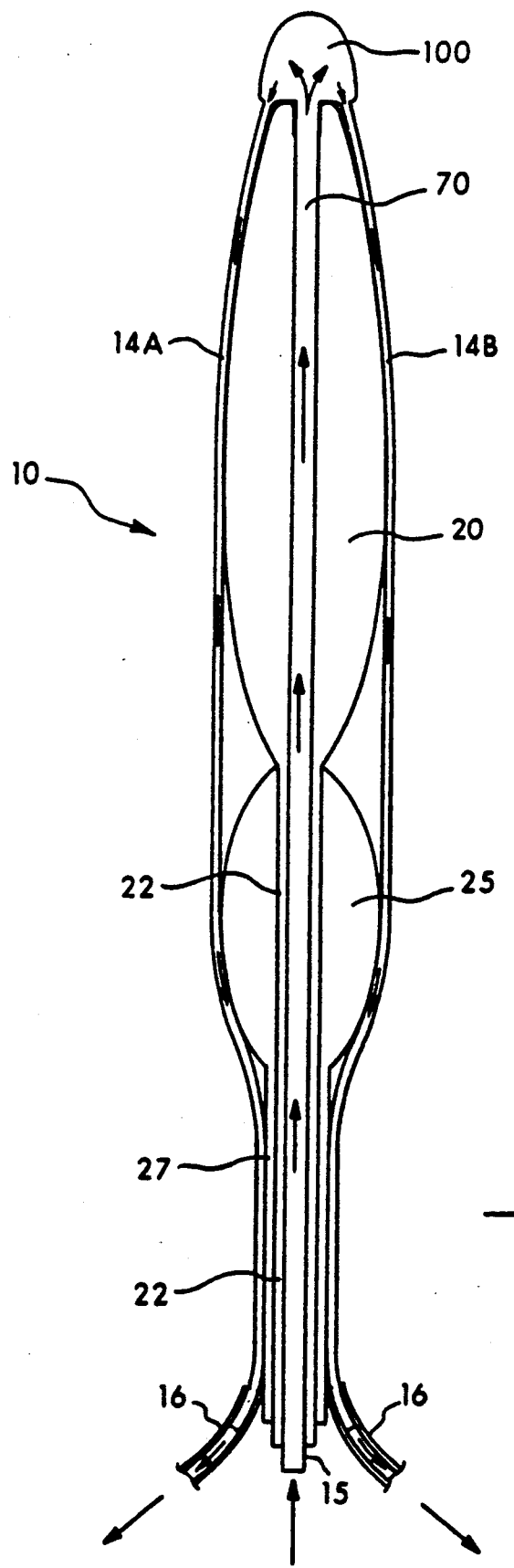
FIG. 10 is a cross-sectional view of yet another alternative embodiment of an oxygenator for practicing the method of the present invention in which two balloons are inflated and deflated asynchronously.

FIG. 10 shows yet another alternative embodiment of an oxygenator which could be used to practice the method of the present invention. In this embodiment, a second inflation balloon 25 has been added adjacent to the first inflation balloon 20. This second balloon 25 has a separate lumen 27 extending through the connector 12 to permit separate inflation and deflation of the second balloon 25 independent of the first balloon 20. In this embodiment, the balloons 20 and 25 will typically be inflated asynchronously (i.e., out of phase with one another) so that resulting turbulence in the patient's blood stream is maximized.

In accordance with the method of the present invention, the various embodiments of an inflatable oxygenator device can be used in anesthetizing a patient. In one use of such a device, after it has been properly positioned in the vena cava of a patient, nitrous oxide ($N_2O$) is introduced into the membranes with oxygen gas under an appropriate pressure so that the gas mixture can diffuse through the walls of the membranes and into the blood stream. Appropriate pressures for delivering the gas mixture to the membranes and the concentrations of the nitrous oxide are variables which may depend upon a number of factors including the size and weight of the patient. It is important that the gas mixture not be delivered under such a pressure that the gas bubbles through the walls of the membranes, however, and accordingly, the use of vacuum at the opposite end of the membranes from where the gas is delivered will in all likelihood be desirable.

It is anticipated that the fibers can be blocked at the end opposite that at which the gas mixture is introduced and the gas mixture delivered at a relatively low pressure which causes the gas to ultimately diffuse through the wall of the membranes without bubbling therethrough.

In an alternative arrangement, a conventional vaporizer (not shown) is placed in the gas passageway between a source of oxygen gas and the intravenous oxygenator itself such that liquid anesthetic agents can be vaporized in a conventional manner and introduced into the flow of oxygen via the vaporizer. Gases such as isoflurane and halothane are examples of gases that can be vaporized and added to oxygen gas delivered to the membrane oxygenator to anesthetize the patient. Concentrations of the vaporized gas are controlled by volume of liquid anesthetic added to the vaporizer. Final gas concentrations will be in the range of 0.5 to 3.0% halothane, isoflurane or similar anesthetic gases that are currently under development. The delivered doses of anesthetic would depend on the flow rate and pressure of the gas stream, as well as the diffusion rate of the anesthetic gases across the hollow fiber membranes.

While the intravenous oxygenator could be used to practice the method of the present invention with most patients, it is anticipated that its primary use would be in situations where an intravenous membrane oxygenator is being used conventionally to augment respiration of a patient so that it is already in place and can be easily converted to use as an anesthetic delivery device without further discomforting the patient.

Although the present invention has been described with a certain degree of particularity, it understood that the present disclosure has been made by way of example, and changes in detail or structure may be made without departing from the spirit of the invention as defined in the appended claims.

I claim:

1. A method of anesthetizing a patient comprising the steps of:
   providing a plurality of gas permeable tubes,
   providing means for injecting an anesthetizing gas into the tubes,
   inserting the tubes within a blood vessel, and
   injecting an anesthetizing gas into the tubes so that the gas can diffuse through the tubes into the blood stream to anesthetize the patient.

2. The method of claim 1 wherein the tubes have opposite open ends and wherein the anesthetizing gas is injected into one of the open ends and further including the step of applying a vacuum at the other open end of the tubes to pull the anesthetizing gas through the tubes.

3. The method of claim 2 wherein the tubes are inserted through a single incision in the blood vessel.

4. The method of claim 1 further including the steps of providing a gas line to the tubes, providing a vaporizer in said gas line, passing oxygen through said gas line while vaporizing a liquid anesthetic agent in said vaporizer such that said oxygen carries said vaporized anesthetic into the tubes.

5. The method of claim 4 further including the step of controlling the concentration of gas delivered to the tubes by controlling the volume of liquid anesthetic delivered to said vaporizer.

6. The method of claim 5 wherein the concentration of the gas delivered to the tubes is in the range of 0.5 to 3.0% anesthetic agent.

7. The method of claim 5 wherein said tubes have opposite open ends and wherein the anesthetizing gas is injected into one of the open ends and further including the step of applying a vacuum at the other open end of the tubes to pull the anesthetizing gas through the tubes.

* * * * *

UNITED STATES PATENT AND TRADEMARK OFFICE
CERTIFICATE OF CORRECTION

PATENT NO. : 5,207,640

DATED : May 4, 1993

INVENTOR(S) : BRACK G. HATTLER, of Pittsburgh, Pennsylvania

It is certified that error appears in the above—identified patent and that said Letters Patent is hereby corrected as shown below:

Cover Page, [56] References
Cited, Other Publications:   "--(International Publication No. WO 91/069642) Applicant: Cardi7--" should read -- (International Publication No. WO 91/09642) Applicant: Cardi- --

Cover Page, [57] Abstract,
at line 3 of paragraph:   "--onto--" should read -- into --

Signed and Sealed this

Eleventh Day of January, 1994

*Attest:*

BRUCE LEHMAN

*Attesting Officer*   *Commissioner of Patents and Trademarks*